(12) United States Patent
Clouatre et al.

(10) Patent No.: US 6,207,714 B1
(45) Date of Patent: Mar. 27, 2001

(54) METHODS AND PHARMACEUTICAL PREPARATIONS FOR IMPROVING GLUCOSE METABOLISM WITH (−)-HYDROXYCITRIC ACID

(76) Inventors: Dallas L. Clouatre, 555 Bryant St #357, Palo Alto, CA (US) 94301-1704; James M. Dunn, 3236 Hinsdale Pl., Littleton, CO (US) 80112

( * ) Notice: Subject to any disclaimer, the term of this patent is extended or adjusted under 35 U.S.C. 154(b) by 0 days.

(21) Appl. No.: 09/661,588

(22) Filed: Sep. 14, 2000

Related U.S. Application Data
(60) Provisional application No. 60/153,840, filed on Sep. 14, 1999.

(51) Int. Cl.[7] ................................................ A61K 31/19
(52) U.S. Cl. .............................................................. 514/574
(58) Field of Search ............................................ 514/574

(56) References Cited

U.S. PATENT DOCUMENTS 3,764,692 * 10/1973 Lowenstein ........................... 424/279
5,626,849 * 5/1997 Hastings et al. .................. 424/195.1
5,783,603 * 7/1998 Majeed et al. ........................ 514/574
5,914,326 * 6/1999 McCarty et al. ..................... 514/188

* cited by examiner

Primary Examiner—Raymond Henley, III

(57) ABSTRACT

A method whereby the glucose metabolism in an individual showing evidence of dysregulation, as is found in insulin resistance, reactive hyperglycemia and/or elevated blood sugar levels and/or diabetes, is improved when that person receives an appropriate oral administration of (−)-hydroxycitric acid. The potassium salt of (−)-hydroxycitric acid is the preferred form of the compound, followed by the sodium salt. The regulation of glucose levels over any given period of time may be improved with a controlled release form of (−)-hydroxycitric acid. Controlled release can be used to provide a sustained and modulated amount of the active to the body as desired and therefore regulate the use of the compound as a hypoglycemic agent.

12 Claims, No Drawings

METHODS AND PHARMACEUTICAL PREPARATIONS FOR IMPROVING GLUCOSE METABOLISM WITH (−)-HYDROXYCITRIC ACID

PROVISIONAL PATENT APPLICATION FILING

This application is entitled to the benefit of Provisional Patent Application Ser. No. 60/153,840 filed Sept. 14, 1999, "Methods And Pharmaceutical Preparations For Improving Glucose Metabolism With (−)-Hydroxycitric Acid"

RELATED PATENT APPLICATION BY THE SAME INVENTORS

Potassium (−)-Hydroxycitric Acid Methods For Pharmaceutical Preparations For Stable And Controlled Delivery

BACKGROUND OF THE INVENTION

1. Field Of The Invention

This invention relates to pharmaceutical compositions containing (−)-hydroxycitric acid useful for lowering elevated blood sugar levels and for improving glucose metabolism in individuals in need thereof.

2. Description Of Prior Art

Elevated and erratic blood sugar levels are components of the condition known as diabetes mellitus. This condition can be life-threatening and high glucose levels in the blood plasma (hyperglycemia) can lead to a number of chronic diabetes syndromes, for example, atherosclerosis, microangiopathy, peripheral neuropathy, kidney disorders and renal failure, cardiac disease, diabetic retinopathy and other ocular disorders, including blindness. A precursor to this condition, insulin resistance, may be a component in many age-related deteriorations and can result in alternating periods of both high and low blood sugar, uneven energy, obesity, hypertension and other disorders.

Diabetic conditions usually are treated medically in one of two ways. Insulin, the hormone which removes glucose from circulation, is supplied exogenously to treat the more severe cases in which the body's ability to produce this hormone is either impaired or nonexistent. Oral diabetes medications (such as sulphonylureas and biguanides) are also available. The drug metformin, a biguanide which is perhaps the safest and most successful of the usual oral hypoglycaemics, suppresses an elevated rate of basal hepatic glucose production. This mode of action in one of the more successful hypoglycaemic drugs underscores the fact that the inability to regulate and suppress hepatic glucose production is an important aspect of diabetes and prodiabetic conditions.

(−)-Hydroxycitric acid (abbreviated herein as HCA) a naturally-ocurring substance found chiefly in fruits of the species of Garcinia, and several synthetic derivatives of citric acid have been investigated extensively in regard to their ability to inhibit the production of fatty acids from carbohydrates, to suppress appetite, and to inhibit weight gain. (Sullivan, A. C., et al., American Journal of Clinical Nutrition 1977;30:767.) HCA has not previously been suggested as a compound with the ability to lower blood sugar levels and/or improve glucose metabolism.

Weight loss benefits were first ascribed to HCA, its salts and its lactone in U.S. Pat. No. 3,764,692 granted to John M. Lowenstein in 1973. The claimed mechanisms of action for HCA, most of which were originally put forth by researcher at the pharmaceutical film of Hoffmann-La Roche, have been summarized in at least two United States Patents. In U.S. Pat. No. 5,626,849 these mechanisms are given as follows: "(−) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis . . . (−) HCA also increases the clearance of LDL cholesterol . . . " U.S. Pat. No. 5,783,603 further argues that HCA serves to disinhibit the metabolic breakdown and oxidation of stored fat for fuel via its effects upon the compound malonyl CoA and that gluconeogenesis takes place as a result of this action. The position that HCA acts to unleash fatty acid oxidation by negating the effects of malonyl CoA with gluconeogenesis as a consequence (McCarty M F. Medical Hypotheses 1994;42:215–225) is maintained in U.S. Pat. No. 5,914,326.

Quite surprisingly, one pronounced effect of HCA—its hypoglycemic effect—has never been mentioned in the literature on the topic. Indeed, those who uphold that HCA is gluconeogenic in its actions and primarily useful for increasing ketogenesis, typically view it as potentially raising blood sugar levels rather than reducing them. The original pharmaceutical research on HCA performed at Hoffman-La Roche mentioned above failed to find significant changes in either blood glucose levels or blood insulin levels, undoubtedly in large part due to the fact that almost all of that research used diets which consisted largely of glucose (e.g., 70% glucose diets were typically employed to encourage lipogenesis).

Whether HCA influences blood sugar levels is of great importance for several reasons, two of which are of particular significance for the use of HCA. First, many or even most individuals with serious weight control issues are insulin resistant and maintain proper glucose control only through the release of elevated amounts of insulin. Second, a large fraction of diabetics are also obese. (DeFronzo R A, Ferinimmi E. Diabetes Care 1991;14:173–194.) Many researchers consider insulin resistance both a cause and an effect of excessive weight. It is a cause due to its impact, for instance, upon the body's ability to metabolize fatty acids for fuel. It is an effect due to the the often demonstrated actions of excessive weight in sustaining the conditions which are linked to the emergence of insulin resistance. (Cusin, Isabelle, et al., International Journal of Obesity 1992;16, Suppl. 4:S1–S11; Ravussin, Eric and Swinburn, Boyd A., The Lancet 1992;340:404–408.) If HCA can aid in the metabolic control of blood glucose levels, it can be used to help break this vicious cycle of insulin resistance found in both obesity and diabetes.

There is evidence from animal studies, but not from any good human study, that ingested HCA will lower blood lipids levels, and it is known that high levels of circulating free fatty acids are often related to insulin resistance and thereby to erratic blood glucose control. However, this is an indirect effect rather than a direct one; it is analogous to maintaining—accurately—that substantial weight loss improves insulin resistance in many individuals. However, neither of these effects (lowering of blood lipids and weight loss), both of which are ascribed to HCA in the literature, are what is defined medically as a hypoglycemic effect.

Hypoglycemic agents have direct effects upon blood glucose levels, often by inhibiting gluconeogenesis. The compound metformin is a classic example of of a hypoglycemic agent which reduces elevated rates of hepatic gluconeogenesis. Such an effect has never been suggested in the literature on HCA to be part of that compound's mode of action. Indeed, a very recent review which suggests the use of HCA as a component in the nutritional therapy for diabetes continues to focus entirely upon a reduction in serum free fatty acids with a likely increase in gluconeogenesis which must be counterbalanced by the ingestion of items such as chromium, biotin or metformin. (McCarty M F. Med Hypotheses 2000 Mar;54(3):483–487; U.S. Pat. No. 5,914,326.)

Only the potassium and sodium salts of HCA are absorbed well enough to be effective hypoglycemic agents at tolerable levels of ingestion. Reasons for this are given in the copending U.S. Patent Application "Potassium (−)-Hydroxycitric Acid Methods For Pharmaceutical Preparations For Stable And Controlled Delivery." The calcium salt of HCA is extremely widely sold in the United States in dosages ranging up to approximately 12 grams per day (providing roughly 6 grams of HCA), and yet there are no reports in the literature of this salt being useful as a hypoglycemic agent.

In contrast to experiences with the calcium salt, the impact of ingestion of appropriate amounts of the appropriate salts of HCA upon subjects with elevated blood sugars is to reduce serum glucose levels, potentially very rapidly. This is particularly important to those suffering from non-insulin-dependent diabetes mellitus (NIDDM); simultaneous storage and release of glucose is an aspect of this condition. Diabetics Type 1 can also be insulin resistant, and it may be possible to use HCA as a blood sugar lowering agent for these patients so as to reduce overall insulin usage inasmuch as elevated amounts of insulin are themselves damaging to the body. In other words, HCA might be used as a hypogylcemic agent for diabetes and in other conditions related to the "metabolic syndrome," also called "Syndrome X" and insulin resistance. No prior art suggests this type of effect upon glucose metabolism.

SUMMARY OF THE INVENTION

The inventors have made the surprising discovery that the glucose metabolism in an individual showing evidence of dysregulation, as is found in insulin resistance and diabetes, is improved when that person receives an appropriate oral administration of (−)-hydroxycitric acid. In the appropriate form(s) and amounts, the compound acts as a hypoglycemic agent. It also reduces reactive hypoglycemia in those who are insulin resistant, albeit it may take several weeks for this effect to be fully realized. The potassium salt of (−)-hydroxycitric acid is the preferred form of the compound, followed by the sodium salt. The regulation of glucose levels over any given period of time may be improved with a controlled release form of HCA. Controlled release can be used to provide a sustained and modulated amount of the active to the body as desired.

Objects and Advantages

It is an objective of the present invention to provide a method of for treating or ameliorating diabetes or insulin resistance by providing a means of reducing elevated blood sugar levels. It is a further object of the present invention to provide a means of stabilizing blood sugar levels so as to avoid reactive hypoglycemia and to otherwise improve blood sugar metabolism. Knowledge of the present invention has the advantages of allowing the use of forms of (−)hydroxycitric acid as anti-diabetics drugs, for lowering elevated blood sugar levels, for stabilizing fluctuating blood sugar levels, and thereby for reducing elements of insulin resistance, including especially through controlled release formulations. A further advantage of the present invention is to allow the employment of effective amounts of HCA for weight loss and other purposes without posing a danger to diabetics which would otherwise arise through ignorance of the hypoglycemic actions of the compound.

DESCRIPTION OF THE PREFERRED EMBODIMENTS

The free acid form and various salts of (−)-hydroxycitric acid (calcium, magnesium, potassium and sodium) have been available commercially for several years. Any of these materials can be used to fulfill the invention revealed here, but with varying degrees of success. For reasons given in our copending U.S. Patent Applicaton "Potassium (−)-Hydroxycitric Acid Methods For Pharmaceutical Preparations For Stable And Controlled Delivery," these materials are generally useful in this descending order of efficacy: potassium salt, sodium salt, free acid, magnesium salt, calcium salt. A novel method for improving the efficacy and workability of these forms is provided in that application. Exact dosing will depend upon the form of HCA used, the weight of the individual involved, and the other components of the diet. Due to the need to control the release of this hypoglycemic agent in diabetics, a controlled release preparation is to be preferred.

EXAMPLE 1

A multi-week pilot open clinical weight loss trial with extremely obese patients was planned to gauge the effects of a pouch delivery form of a potassium salt of (−)-hydroxycitrate under the normal circumstances faced in clinical practice with this patient population. Fourteen patients were enrolled, three of whom were diabetics on medications and several others who were suspected of suffering from insulin resistance. The patients ingested 3–4 grams of HCA per day in two divided doses. Aside from being informed that they must eat a carbohydrate-containing meal within one hour of taking the HCA and that they should avoid eating late in the day, they were not instructed to follow any special diet or exercise plan outside their normal habits and no caloric restriction was imposed. This particular form of potassium (−)-hydroxycitrate delivery typically was mixed into water or juice and consumed at mid-morning and mid-afternoon. The delivery was a water-soluble immediate release form. It was a pre-commercial preparation and nearly all of the patients complained regarding the inconvenience and poor taste of the product, albeit there were no other issues of tolerability. A number of patients continued on the program for 6 weeks. However, comparative data was good for only 3 weeks because two of the diagnosed diabetics experienced hypoglycemic reactions. Several other patients experienced good appetite suppression, yet also complained off episodic tiredness at the beginning of the program, a sign of low blood sugar. Two patients subsequently were placed on phentermine. One patient who followed the program for 10 weeks with excellent weight loss (32 pounds over 10 weeks) found that his tendency toward elevated blood sugar was stabilized during the program. This patient returned to his prior experiences of infrequent hypoglycemia roughly one week after he had left the program, something which suggests a carryover effect from the compound. The average weight loss over the 3 week period for these patients was approximately 3 pounds per person per week. The clinical decision was made that potassium (−)-hydroxycitrate in an immediate release format can exercise a strong hypoglycemic effect in diabetics and that it appears to influence blood sugar levels in protodiabetics, as well. At therapeutically effective dosages, HCA probably should be used with diabetic populations only under a physician's care.

EXAMPLE 2

The results in Example 1 were unexpected from the published literature on HCA. Our clinical experience was that as little as 3 grams of HCA per day in the form of potassium (−)-hydroxycitrate (5 grams of the salt) may exert a significant hypoglycemic effect in diabetics. As a crude test of whether this hypoglycemic effect might be experienced with other forms of HCA, an individual with suspected insulin resistance was given approximately 15 grams of calcium (−)-hydroxycitrate in two divided dosings per day for one week. This individual experienced appetite suppression and weight loss, but also symptoms of low blood sugar. Results were in line with our other clinical experience that the potassium salt of HCA is at least 300% more efficacious than is the calcium salt.

EXAMPLE 3

The results in Example 2 led us to question whether a relatively large dose of HCA might affect blood sugar levels in an individual whose blood sugar is in the low normal range. A dose of 1.5 grams HCA derived from potassium (−)-hydroxycitrate and delivered in a special coated form designed to bypass interaction with stomach acids and to release only in the higher pH of the small intestine was used. After an overnight fast, the subject had a measured blood glucose level of 85 mg/dL. Subject ate a 500 calorie breakfast which included the experimental HCA. Two hours after this meal, subject's blood glucose level had dropped to 77 mg/dL. Subject reported no changes in energy levels, but this subject was known to metabolize fats well as fuel, hence was not expected to experience low energy. The result with this subject helps to explain why some, but not most individuals who experience reduced blood sugar with an appropriate dose of HCA may experience some initial tiredness, i.e., insulin resistance interferes with the ability to metabolize fats for energy. In a non-diabetic, once the body returns to a more normal ability to metabolize fats as a fuel source, the low blood sugar symptoms disappear.

CONCLUSIONS (−)-Hydroxycitrate has a multitude of metabolic functions. The literature teaches that the compound reduces blood lipids, induces weight loss and decreases appetite in both animals and humans. However, the inventors have discovered that this compound is also a hypoglycemic agent or anti-diabetic agent. This is an entirely novel use of HCA in its free acid and its salt forms.

We claim:

1. A method for treating or ameliorating diabetes or insulin resistance by lowering elevated blood sugar levels in individuals in need thereof which is comprised of administering orally an effective amount of (−)-hydroxycitric acid.

2. A method for treating or ameliorating diabetes or insulin resistance by improving glucose metabolism in individuals in need thereof which is comprised of administering orally to such individuals an effective amount of (−)-hydroxycitric acid.

3. The method of claim 1 where the (−)-hydroxycitric acid is supplied as a therapeutically effective amount of the free acid.

4. The method of claim 1 where the (−)-hydroxycitric acid is supplied as a therapeutically effective amount of the alkali metal salts potassium or sodium (−)-hydroxycitrate.

5. The method of claim 1 where the (−)-hydroxycitric acid is supplied as a therapeutically effective amount of the alkaline earth metal salts calcium or magnesium (−)-hydroxycitrate.

6. The method of claim 1 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate.

7. The method of claim 1 where the (−)-hydroxycitric acid is supplied as a therapeutically effective amount as the free acid or as one or more of the salts of the free acid and is delivered in a controlled release form.

8. The method of claim 2 where the (−)-hydroxycitric acid is supplied as a therapeutically effective amount of the free acid.

9. The method of claim 2 where the (−)-hydroxycitric acid is supplied as a therapeutically effective amount of the alkali metal salts potassium or sodium (−)-hydroxycitrate.

10. The method of claim 2 where the (−)-hydroxycitric acid is supplied as a therapeutically effective amount of the alkaline earth metal salts calcium or magnesium (−)-hydroxycitrate.

11. The method of claim 2 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate.

12. The method of claim 2 where the (−)-hydroxycitric acid is supplied as a therapeutically effective amount as the free acid or as one or more of the salts of the free acid and is delivered in a controlled release form.

* * * * *